(12) United States Patent
Aoe et al.

(10) Patent No.: US 11,612,318 B2
(45) Date of Patent: Mar. 28, 2023

(54) HANDHELD AND SLIT LAMP DETACHABLE CAMERA WITH PIVOTABLE ARM

(71) Applicant: Box Medical Solutions, Inc., Thousand Oaks, CA (US)

(72) Inventors: Andy Aoe, West Hills, CA (US); Mann Trinh, West Hills, CA (US); Viktor Kapiliovich, Southampton, PA (US)

(73) Assignee: Box Medical Solutions, Inc., Thousand Oaks, CA (US)

( * ) Notice: Subject to any disclaimer, the term of this patent is extended or adjusted under 35 U.S.C. 154(b) by 389 days.

(21) Appl. No.: 16/812,299

(22) Filed: Mar. 7, 2020

(65) Prior Publication Data

US 2020/0305710 A1    Oct. 1, 2020

Related U.S. Application Data

(60) Provisional application No. 62/827,143, filed on Mar. 31, 2019.

(51) Int. Cl.

| | |
|---|---|
| *A61B 3/135* | (2006.01) |
| *A61B 3/14* | (2006.01) |
| *A61B 3/12* | (2006.01) |
| *G16H 50/20* | (2018.01) |
| *G16H 30/40* | (2018.01) |
| *G16H 10/60* | (2018.01) |

(52) U.S. Cl.
CPC ............ *A61B 3/135* (2013.01); *A61B 3/1208* (2013.01); *A61B 3/145* (2013.01); *G16H 10/60* (2018.01); *G16H 30/40* (2018.01); *G16H 50/20* (2018.01)

(58) Field of Classification Search
CPC .......... A61B 3/135; A61B 3/1208; A61B 3/14
USPC ................................................... 351/214, 221
See application file for complete search history.

(56) References Cited

U.S. PATENT DOCUMENTS

| | | | | |
|---|---|---|---|---|
| 4,175,839 | A | * | 11/1979 | Muller ................. A61B 3/0075 351/245 |
| 4,504,129 | A | * | 3/1985 | Van Iderstine ........ A61B 3/135 351/221 |
| 4,801,198 | A | * | 1/1989 | Heacock ............. A61F 9/00821 359/676 |

(Continued)

OTHER PUBLICATIONS

Hecht, Eugene. Optics. Hecht, Addison-Wesley, Reading, MA, 1998, pp. 49 (Year: 1998).*

*Primary Examiner* — Zachary W Wilkes

(57) ABSTRACT

A clinician eye camera apparatus, networked system, and medium to record eye images using the three different types of light to diagnose different medical conditions/disorders, comprising: 1) a camera unit housing a) a front PCB with a plurality of LED's and a middle aperture to fit a rear camera lens; b) a middle camera filter unit, comprising a plurality of light filters, and a servo motor with a propeller that rotates the light filters into position in front of a rear camera lens; c) the rear camera lens; and 2) a pivotable arm assembly comprising a top end unit attachable to the camera unit, and a middle handle unit pivotably attached to an arm unit. The arm assembly can be used in a straight handheld mode; or bent 90 degrees for mounting in a slit lamp. Images are transmitted to a clinician computer and/or a remoter server.

20 Claims, 16 Drawing Sheets

(56) References Cited

U.S. PATENT DOCUMENTS

| | | | | |
|---|---|---|---|---|
| 5,363,155 | A * | 11/1994 | Urinowski | A61B 3/0075 |
| | | | | 600/405 |
| 7,052,135 | B2 * | 5/2006 | Takeda | A61B 3/135 |
| | | | | 351/200 |
| 7,083,281 | B2 * | 8/2006 | Yogesan | A61B 3/185 |
| | | | | 351/214 |
| 7,922,329 | B1 * | 4/2011 | Graether | A61B 3/135 |
| | | | | 351/205 |
| 9,357,920 | B2 * | 6/2016 | Yates | A61B 3/14 |
| 9,438,773 | B2 * | 9/2016 | Howes | A61B 3/135 |
| 9,826,901 | B2 * | 11/2017 | Kim | A61B 3/135 |
| 10,575,729 | B2 * | 3/2020 | Li | A61B 3/15 |
| 10,842,373 | B2 * | 11/2020 | Fink | A61B 3/0008 |
| 2005/0041207 | A1 * | 2/2005 | Miller | A61B 3/156 |
| | | | | 351/200 |
| 2012/0320340 | A1 * | 12/2012 | Coleman, III | A61B 3/10 |
| | | | | 351/208 |

* cited by examiner ( PRIOR ART )

HANDHELD AND SLIT LAMP DETACHABLE CAMERA WITH PIVOTABLE ARM

PRIORITY CLAIM

The present invention claims the benefit of priority to U.S. provisional Ser. No. 62/827,143 filed on Mar. 31, 2019, the entire contents of which are hereby incorporated by reference in its entirety.

FIELD OF THE INVENTION

The present invention generally comprises a digital camera mounted on a pivotable arm for use by an ophthalmologist or optometrist in photographing and recording images of a patient's inner and outer eyes.

BACKGROUND OF THE INVENTION

Eye examinations that are conducted by optometrists and ophthalmologists normally require the use of a slit lamp, which are primarily microscopes with bright white lights that provide enhanced views of a patient's inner eye structure. The clinician is able to make a patient diagnosis and recommend a course of treatment based upon the physical examination with the slit lamp views, as well as with the patient history.

Often, though, the slit lamp views are limiting because of the inability to filter out different wave lengths of light to clearly see all inner eye structures.

Slit lamp views should also be digitally recorded in order to store in a patient's medical records evidence of their current eye health, and their history of progress in responding to any prescribed treatment. Prior art slit lamps with built-in cameras are often expensive, and do not allow for a clinician to edit and enhance the images.

What is needed in the industry is a portable, digital camera that is attachable to the slit lamp as an accessory, while enabling the clinician to view the eye from different angles, using different light filters. The camera should allow the clinician to easily record the images (photographs and videos) and store them on computers and servers that allow the clinician to digitally enhance the images in order to more accurately diagnose and track an eye disorder.

SUMMARY OF THE INVENTION

The various embodiments of the present invention comprise eye image recording apparatus and a networked computer system comprising: 1) an eye imaging and recording apparatus with a camera connected to a detachable pivotable handle assembly for use by a clinician to record inner and outer images of a patient's eye; 2) a clinician's electronic computing device; 3) a networked connection; and 4) a cloud server for storing patient's digital images. In an embodiment, a USB cable is used to transmit images from the camera to a computer (e.g. a clinician's laptop, tablet), which can then store them in a clinician's cloud medical file account on a remote server. In another embodiment, the camera comprises a Wi-Fi unit, and the images are transmitted wirelessly to a clinician's computer and/or a remote server.

The eye imaging apparatus further comprises a pivotable arm assembly that comprises: a handle unit that the clinician is able to use to grasp and hold the assembly; and a rotatable arm unit connected to the bottom end of the handle. The assembly has two configurations: handheld mode, which comprises a straight alignment of the handle and arm units; and slit-lamp mode, which has the arm unit rotated 90 degrees (perpendicular) to the handle and inserted into a slit lamp accessory mounting hole. The pivotable arm assembly also comprises a button at the top end to start/stop recording of camera images. The apparatus bottom end of the arm unit further comprises at least one adapter to enable the bottom end to attach to a slit lamp accessory mounting hole.

The present invention further comprises a camera unit for capturing, storing, and transmitting eye photographs and/or videos to a clinician's electronic computer device. In an exemplary embodiment, the camera unit comprises an outer housing (e.g. substantially square-shaped) and internal components comprising: 1) a front printed circuit board (PCB) with a plurality of light emitting diodes and a middle opening to align a rear camera lens; 2) a middle camera filter unit, comprising a plurality of light filters, and a servo motor with a propeller that rotates one light filter into position in front of the rear camera lens; and 3) a rear camera lens connected to a complementary metal oxide semiconductor (CMOS) sensor, a rear printed circuit board (PCB) and a battery.

The front printed circuit board (PCB) further comprises a gyroscope to determine if the apparatus is handheld and moving or is in a fixed position as mounted in a slit lamp. And the front PCB further comprises a blue light emitting diode (LED), a warm white LED, and an infrared LED, to enable the camera unit to capture visible light, infrared light; and visible light without the blue light.

The plurality of light filters comprise: a first filter able to block infrared light and longer wavelengths from being transmitted to the camera lens, and a second filter able to block visible light and shorter wavelengths from being transmitted to the camera lens. In an embodiment, the rear printed circuit board further comprises a memory, and computer-executable program instructions stored in the memory to rotate the light filters into position in front of the rear camera lens, and capture and store camera images by the CMOS sensor.

The camera unit further comprises: a rotatable base and a fixed housing within the middle camera filter unit, wherein the plurality of light filters is mounted on the rotatable base that resides within the fixed housing. The fixed housing further comprises: a top opening for the servo propeller to rotate one of the light filters into position in front of the camera lens; and a middle opening to align with the rear camera lens and one of the light filters. The camera lens is a fixed focal length lens. And the camera unit further comprises: a USB port to transmit commands and camera images to a clinician's electronic computing device.

The present invention further comprises a mobile application running on a clinician's electronic computing device, that is either installed on the device, or accessible via a network. Hence, the present invention further comprises a non-transitory computer readable storage medium with instructions for operation of the camera unit, and for storing of the captured images and/or videos into the patient's digital record.

In an embodiment, the computer program product, comprises: a non-transitory computer-readable storage device having computer-readable program instructions embodied thereon that when executed by a computer cause the computer to transmit and store camera images, the computer-executable program instructions comprising: computer program instructions to: operationally control a clinician eye image recording apparatus to rotate a camera filter into position in front of a camera lens, capture a plurality of camera images of a patient's inner and outer eyes, and transmit the camera images to a clinician's electronic computing device and/or a remote server; wherein the clinician eye image recording apparatus, comprises: a) a camera unit comprising an outer housing, and internal components comprising: 1) a front printed circuit board (PCB) with a plurality of light emitting diodes and a middle opening to fit a rear camera lens; 2) a middle camera filter unit, comprising a plurality of light filters, and a servo motor with a propeller that rotates one light filter into position in front of a rear camera lens; 3) a rear camera lens connected to a complementary metal oxide semiconductor (CMOS) sensor, a rear printed circuit board (PCB), a battery; and, b) a pivotable arm assembly comprising a top end unit attachable to the camera unit, and a middle handle unit pivotably attached to an arm unit.

In the computer program product, the arm unit is rotatable from a first position aligned with the handle unit for a clinician to hold and move the apparatus, and to a second position with the arm unit rotated until it is perpendicular to the handle unit. And, the top unit further comprises a recording button to activate and deactivate the camera unit to record eye images by the computer program product transmitting commands to the rear printed circuit board. And, the front PCB further comprises a blue light emitting diode (LED), a warm white LED, and an infrared LED, to enable the camera unit to capture visible light, infrared light; and visible light without the blue light. And, the plurality of light filters comprise: a first filter able to block infrared light and longer wavelengths from being transmitted to the camera lens, and a second filter able to block visible light and shorter wavelengths from being transmitted to the camera lens.

The present invention further comprises a method of diagnosing and treating a patient with an eye condition, comprising: 1) providing a networked system comprising an eye imaging and recording apparatus; 2) connecting a clinician electronic computing device to the eye imaging and recording apparatus using a USB cable or a wired or wireless network connection; 3) activating a non-transitory computer storage medium on the clinician device and selecting a type of eye examination; 4) activating the camera unit to capture and transmit camera images to the clinician electronic computing device; 5) storing the images in a patient record on a remote or cloud account; 6) diagnosing and treating the patient based upon the camera images, a physical examination and a patient history.

The present invention has significant advantages over the prior art by allowing the clinician to capture eye images in both a fixed position on the slit-lamp, and at various positions that the clinician controls by holding and moving the camera.

The present invention also has significant advantages over the prior art by enabling the recording of images using three different types of light, which can be used to diagnose different medical conditions/disorders: 1) capture visible light; 2) capture infrared (IR) light; and 3) capture visible light without the blue light. The different types of light are created by different colored light emitting diodes on the front PCB and the light filters in the middle camera unit.

A further understanding of the invention, its various embodiments and operating parameters will be apparent with reference to the following drawings and detailed description.

BRIEF DESCRIPTION OF THE DRAWINGS

The above and other features, aspects, and advantages of the present disclosure will become better understood with regard to the following description, appended claims, and accompanying drawing herein.

DETAILED DESCRIPTION OF EXEMPLARY EMBODIMENTS

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

And although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As used herein, the term "assembly" and "unit" and "apparatus" may be used interchangeably.

In various embodiments disclosed herein, as illustrated in FIGS. 1A-5E, the present invention comprises an ophthalmologist and optometrist eye image recording apparatus 100, comprising: a) a camera unit 20 comprising an outer, substantially square housing 22, 24; and b) a pivotable handle-arm unit 30, which in an embodiment, is detachable from the camera unit 20. It is noted that other shapes of the camera housing 22, 24 are envisioned within the scope of the present invention, e.g. by way of non-limiting examples: rectangular, circular, etc. housing.

Figure 1A:
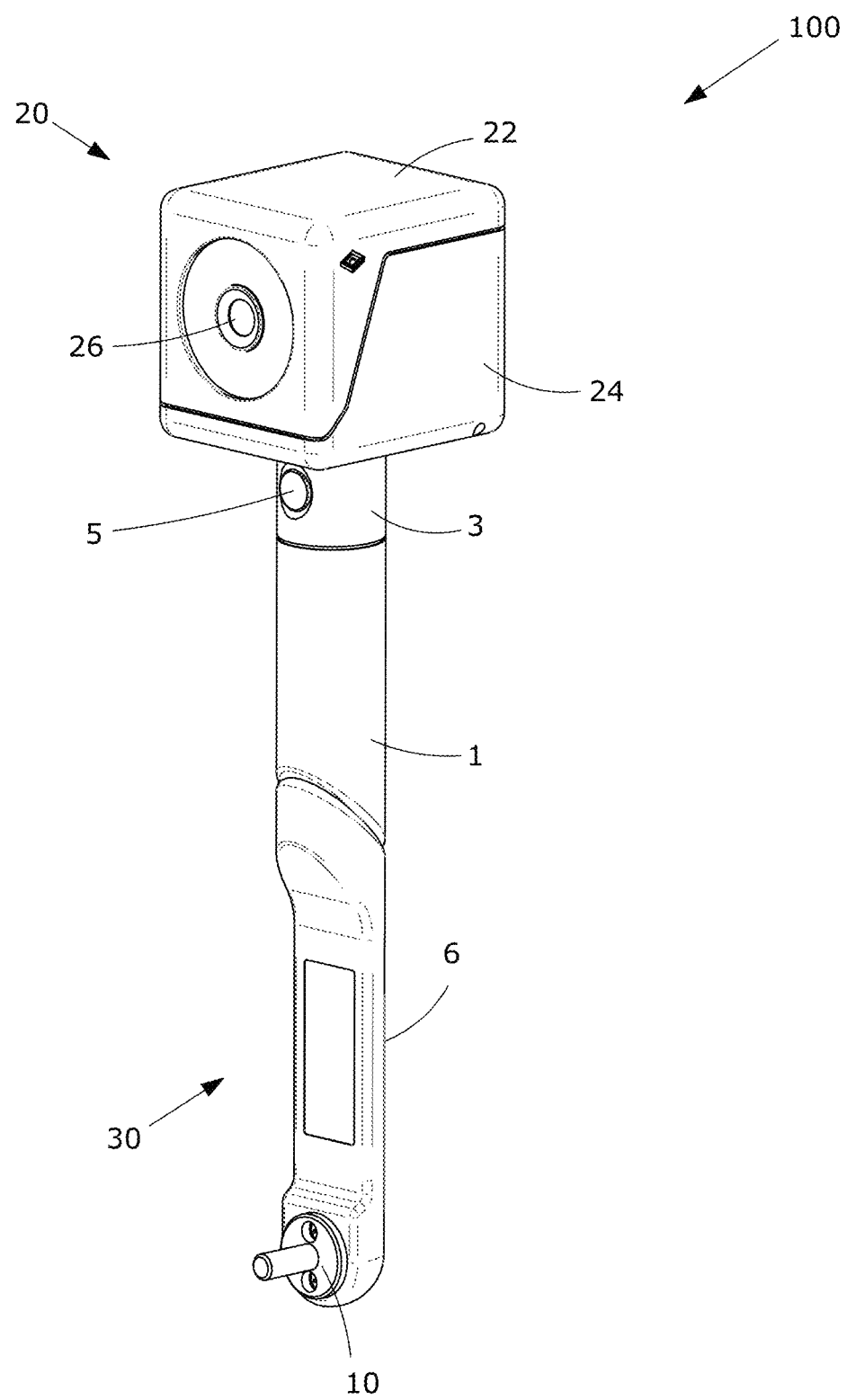
FIG. 1A is a front perspective view of the camera-pivotable arm assembly in the hand-held mode/configuration.
Figure 1B:
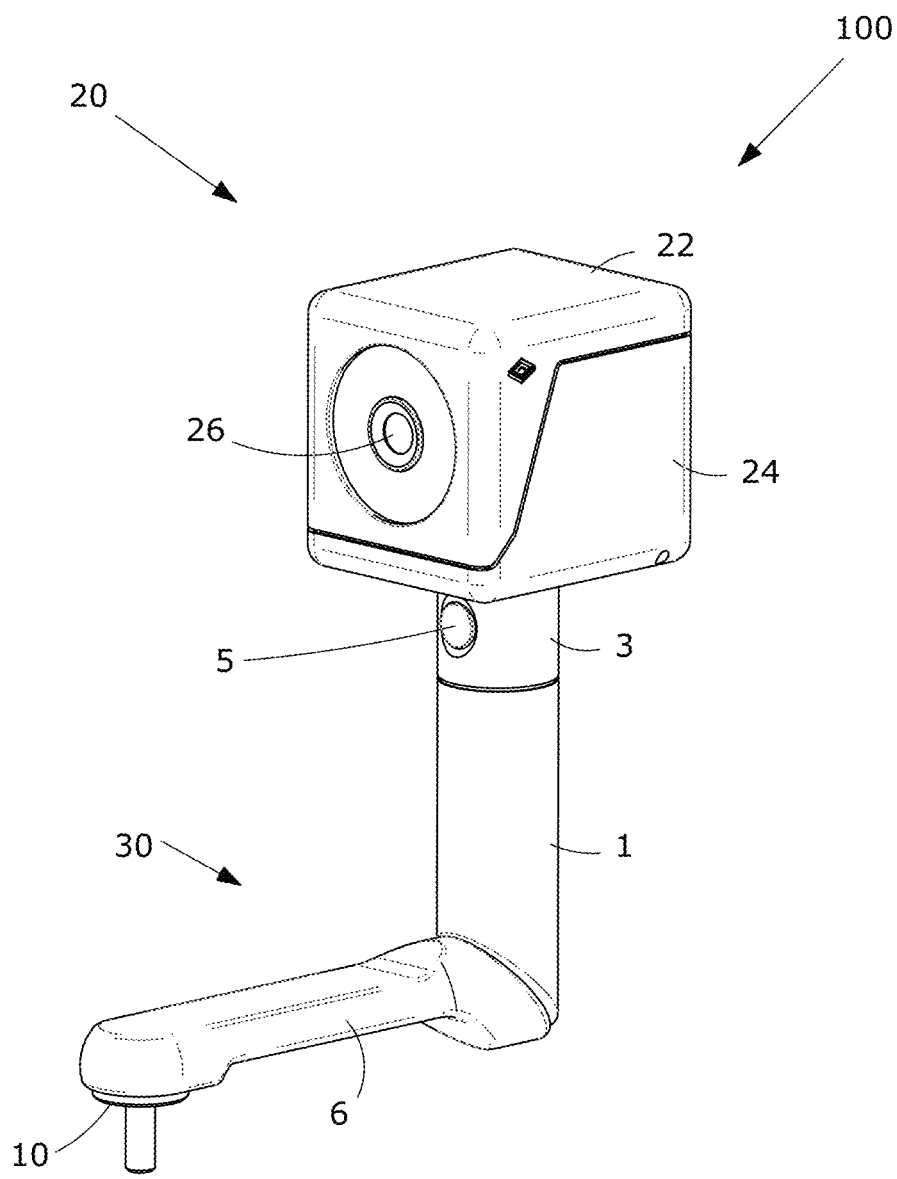
FIG. 1B is a front perspective view of the camera-pivotable arm assembly in the slit lamp configuration.
Figure 3A:
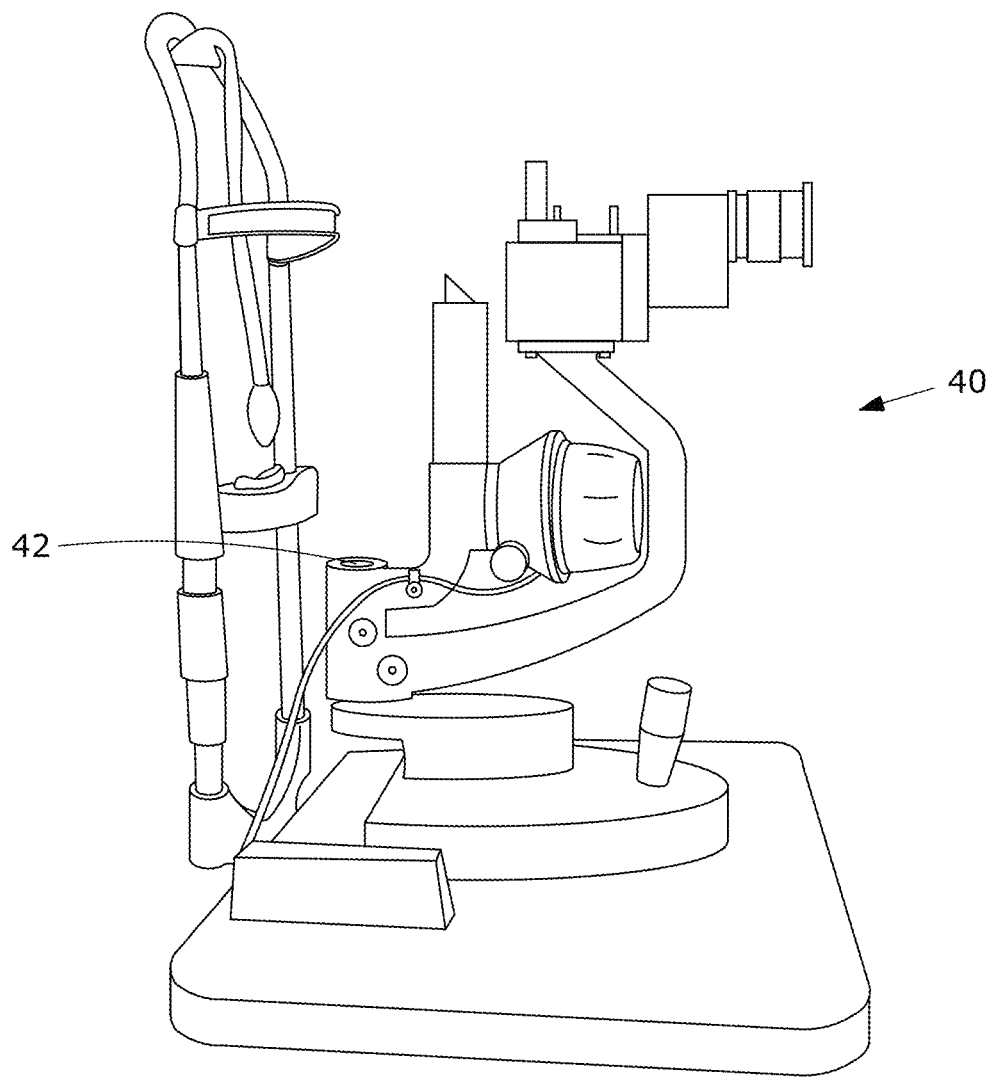
FIG. 3A is a right-side perspective view of a prior art slit lamp apparatus without the camera-pivotable arm assembly mounted; and illustrating the slit lamp accessory mounting hole where the bottom end of the camera-arm assembly is inserted.
Figure 3B:
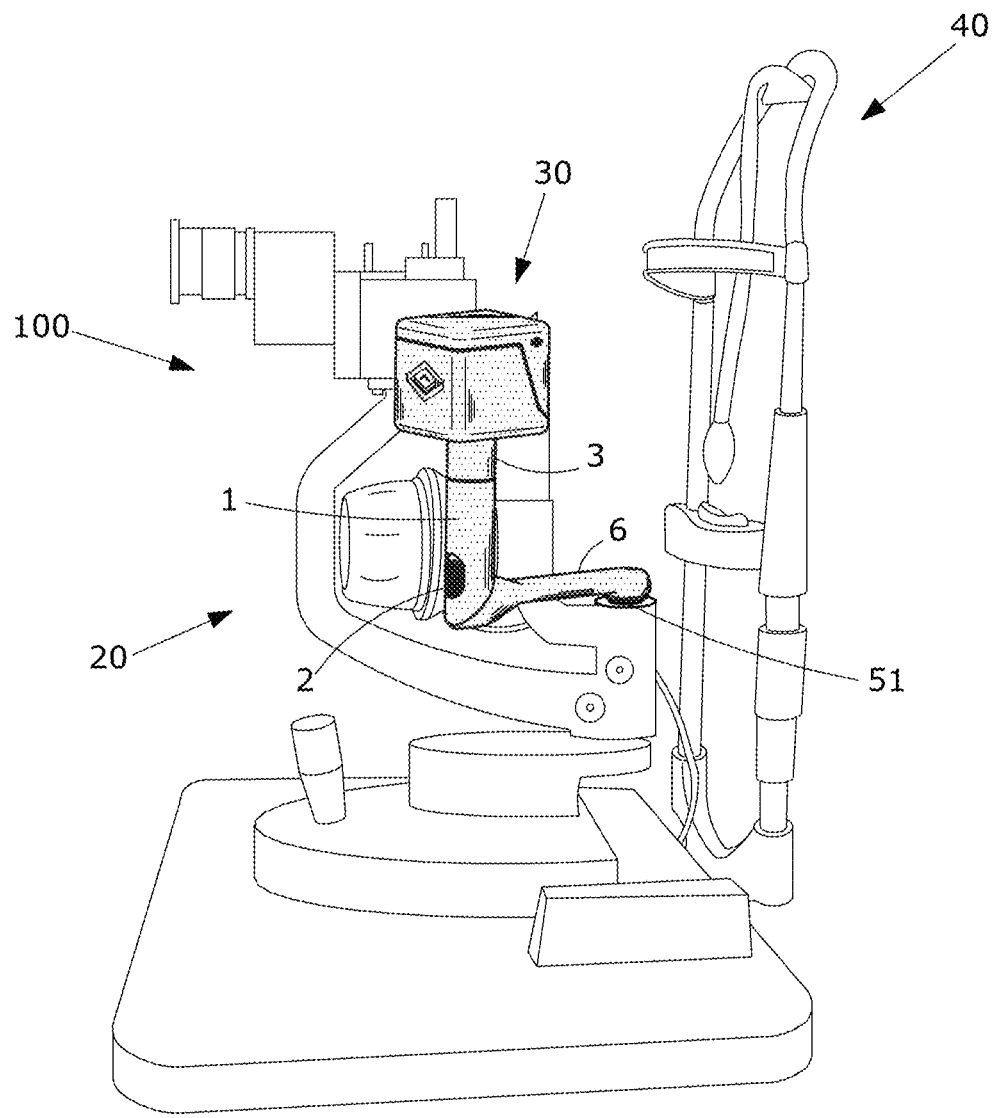
FIG. 3B is a left side perspective view of the slit lamp apparatus with the camera-pivotable arm assembly of the present invention mounted into the slit lamp accessory mounting hole.

The imaging apparatus 100 is able to be used handheld in a substantial "I" shape as illustrated in FIG. 1A; or as an attachment to a slit lamp apparatus 40 with the handle-arm 30 configured into a substantial "L" shape, as illustrated in FIGS. 1B and 3B. A gyroscope 31 on the camera printed circuit board (PCB) 34 detects which configuration the camera unit is being used in: hand-held, or fixed position within a stilt lamp.

The clinician uses the camera-arm assembly in the handheld position to capture images and videos from various angles.

Pivotable Handle-Arm Assembly

As illustrated in FIGS. 1A-2B, the pivotable arm assembly 30 comprises: a handle unit 1 that the clinician is able to grasp and hold the assembly; and a rotatable arm unit 6 connected to the bottom end of the handle 1. In an embodiment illustrated in FIGS. 1A-2B, handle unit 1 is hollow tubular shaped; and rotatable arm unit 6 is substantially tubular shaped on the ends with a substantially flat rectangular shaped midsection.

The arm assembly 30 is rotatable between a handheld mode, comprising the arm unit 6 positioned in line beneath the handle 1 (e.g. 180 degrees alignment), and to a position perpendicular beneath the handle 1 (e.g. 90 degrees alignment) for use in the slit lamp mode. The user is able to move between the two positions by depressing slider 2, i.e. button, on the rear side of the assembly (e.g. see FIGS. 2A and 2B).

Figure 2A:
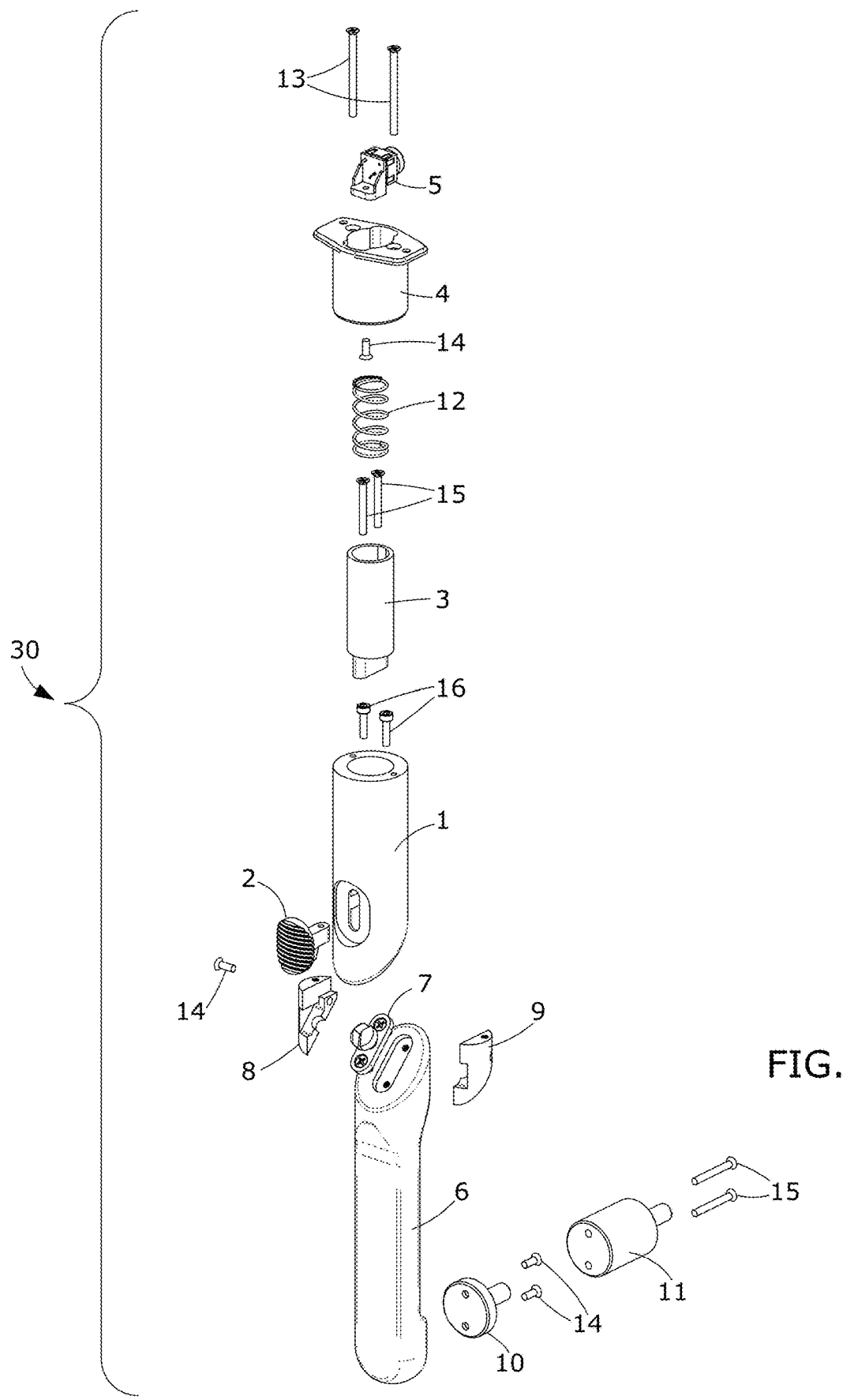
FIG. 2A is an exploded rear perspective view of the camera-pivotable arm assembly in the hand-held mode/configuration and showing the long adapter.
Figure 2B:
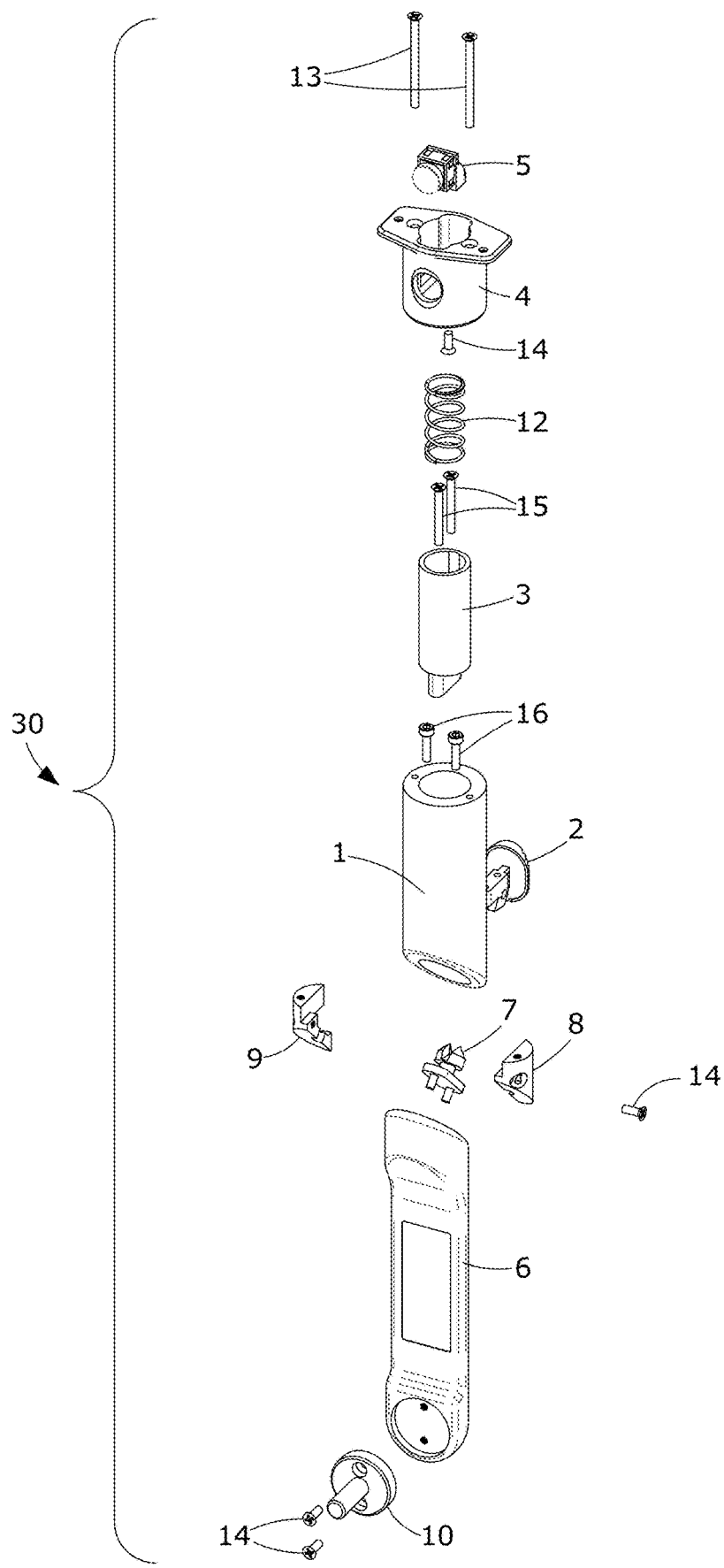
FIG. 2B is an exploded front perspective view of the camera-pivotable arm assembly in the hand-held mode/configuration.

At the top end of arm assembly 30, as shown in FIGS. 2A and 2B, a button 5 is activated to record camera images, which are transmitted in an embodiment via a USB cable to the clinician's computer and/or a remote server for storage in a patient's medical record.

And at the bottom end of assembly 30, as shown in FIGS. 2A-2B, adapter 10 and/or adapter 11 are used to attach the assembly into the slit lamp 40's accessory mounting hole 51 of FIG. 3B.

The pivotable Handle-Arm assembly/unit 30 further comprises the parts shown in Table 1, and the exploded views of FIGS. 2A and 2B.

TABLE 1

| FIG. ITEM NO. | ARM COMPONENTS | QTY. |
|---|---|---|
| 1 | Handle | 1 |
| 2 | Slider/Release Button | 1 |
| 3 | Slider Guide/Top Unit | 1 |
| 4 | Handle Tip | 1 |
| 5 | Recording Button | 1 |
| 6 | Arm | 1 |
| 7 | Arm Axis | 1 |
| 8 | Half of Holding Ring - 1 | 1 |
| 9 | Half of Holding Ring - 2 | 1 |
| 10 | Adapter | 1 |
| 11 | Adapter (long)- alternate to #10 | 1 |
| 12 | Spring, McMaster 9657K338 | 1 |
| 13 | Screws, McMaster 91420A136 | 2 |
| 14 | Screws, McMaster 91420A118 | 4 |
| 15 | Screws, McMaster 91420A130 | 4 |
| 16 | Screws, McMaster 91292A114 | 2 |

Camera Unit

Figure 4A:
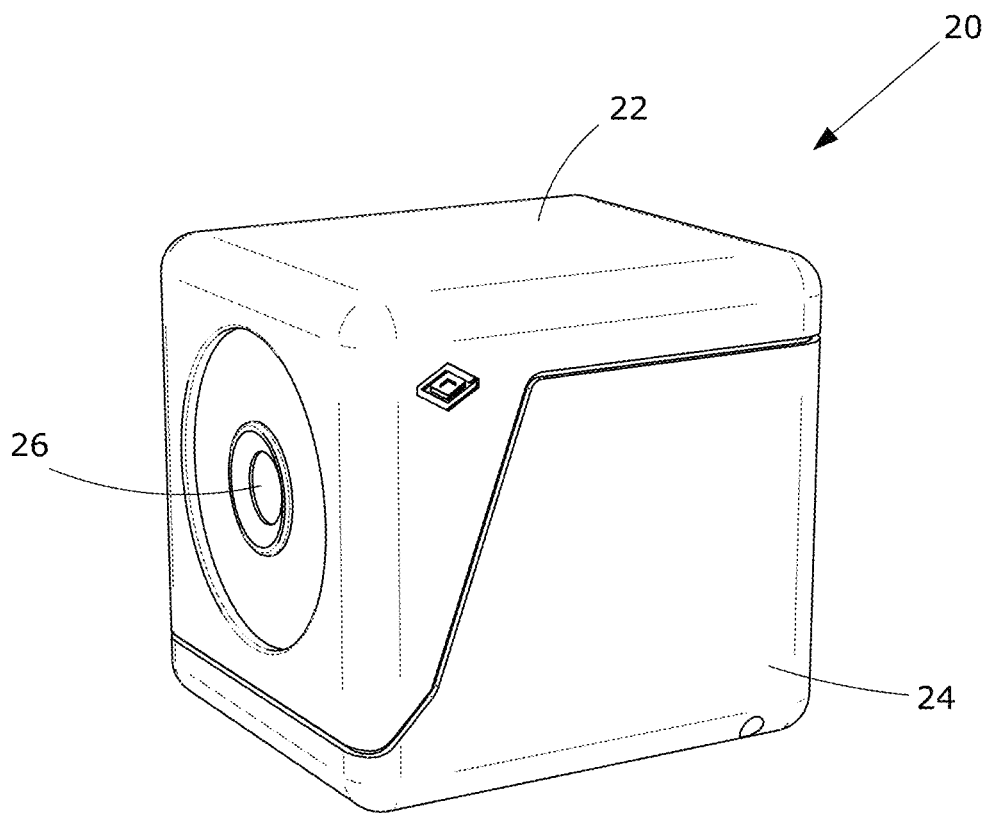
FIG. 4A is front perspective view of an exemplary camera unit of the present invention.
Figure 4B:
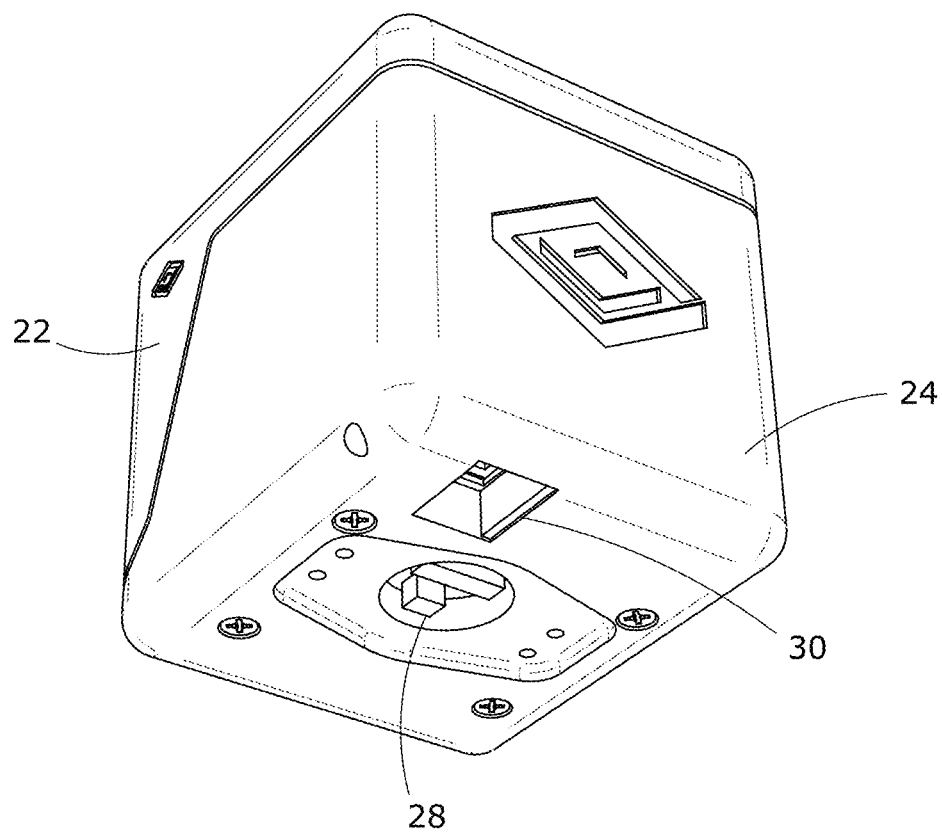
FIG. 4B is a bottom rear perspective view of the exemplary camera unit illustrating the USB port for a cable to connect to a clinician's electronic computing device.
Figure 4C:
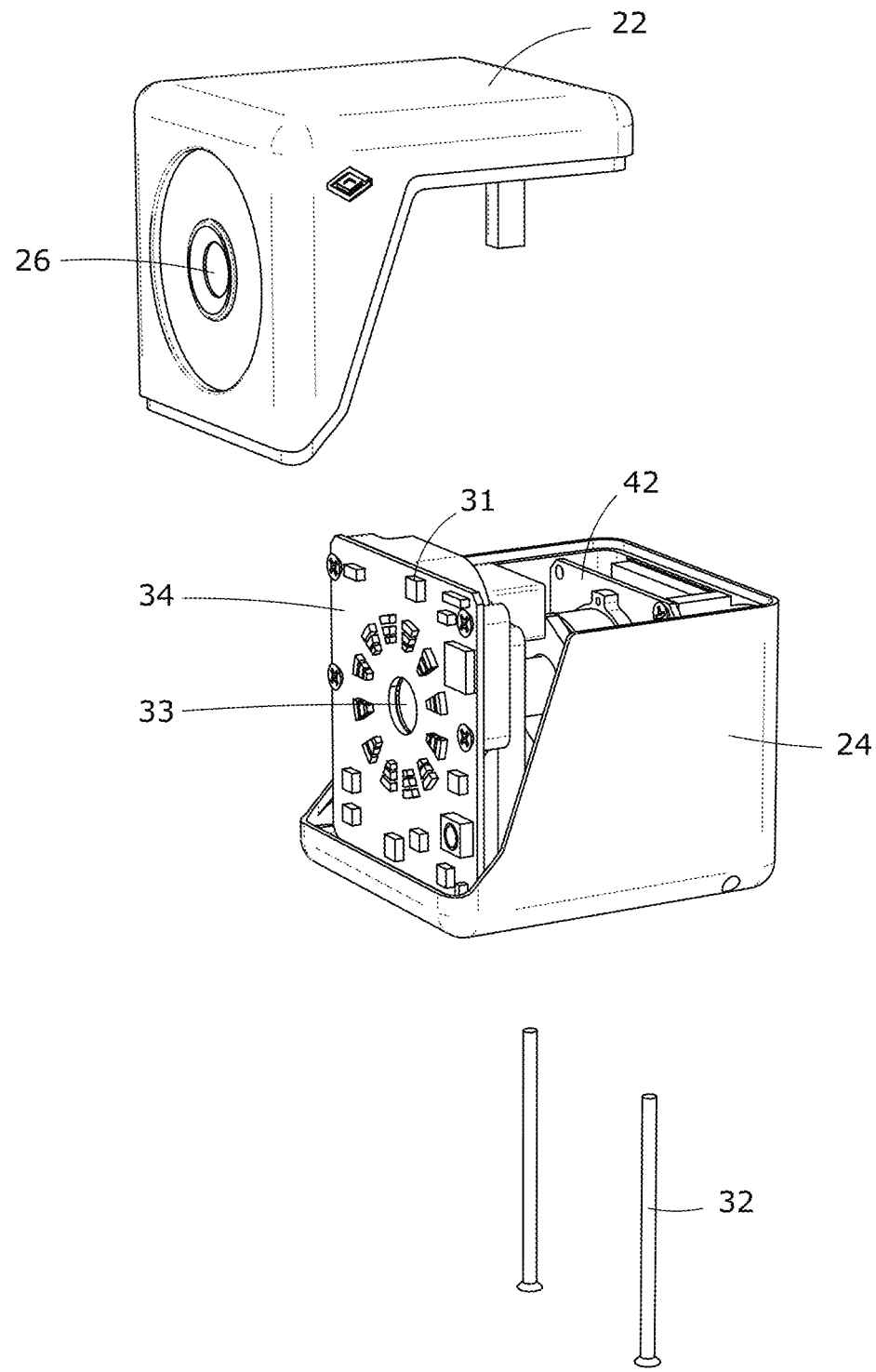
FIG. 4C is an exploded front perspective view of an exemplary camera unit of the present invention illustrating the top and bottom component of the substantially square outer housing; and the inner camera components as assembled.

Housing: An exemplary embodiment of the camera unit 20 is illustrated in FIGS. 4A-4C, and comprises: a substantially squared-shaped outer housing with a top unit 22 covering the top end and the front of the camera with a lens hood comprising a clear glass/plastic cover 26 for the lens (e.g. FIG. 5C, 43); and a bottom unit 24 covering the rear side and the bottom end with a fixation mechanism 28 to snap onto the top end of the arm unit (e.g. FIG. 4B). The bottom unit 24 further comprises a fixation mechanism 30 for connecting a USB cable between the camera unit and the clinician's electronic computing device. In an exemplary embodiment, the camera unit 20 is about 70 millimeters wide, about 83 millimeters in height, and about 80 millimeters in thickness/depth. Table 2 lists the camera components, comprising the outer housing 20, and the inner sections from front to rear: front PCB assembly 70; camera filter assembly 72; and camera lens assembly 74.

TABLE 2

| FIG. ITEM NO. | CAMERA COMPONENTS |
|---|---|
| | Camera Housing 20 |
| 22 | Top Unit |
| 24 | Bottom Unit |
| 26 | Lens Hood/Cover |
| 28 | Snap fix. to arm unit |
| 30 | USB cable connector |
| | Front PCB Unit/Assembly 70 |
| 31 | Gyroscope |
| 32 | Camera Housing Screws |
| 33 | Lens aperture in PCB |
| 34 | LED Printed Circuit Board (PCB) with LED's |
| | Filter Unit/Assembly 72 |
| 35 | Lens aperture |
| 36 | Filter Rotatable Housing/Holder |
| 55 | Propeller aperture in housing 36 |
| 37 | IR Filter 55234 |
| 38 | White Filter 6604 |

TABLE 2-continued

| FIG. ITEM NO. | CAMERA COMPONENTS |
|---|---|
| 39 | Fixed Filter Housing Base |
| 40 | Servo Positioning Motor |
| 41 | Propeller to rotate lens |
| | Lens Unit/Assembly 74 |
| 42 | Camera Printed Circuit Board (PCB) |
| 43 | Camera Lens end- e.g. Edmund optics |
| 44 | CMOS sensor/Bayer filter |
| 45 | Adapter |
| 50 | Battery |

The camera housing 20 covers the camera components, which comprise: 1) a front LED printed circuit board (PCB) 34 with a gyroscope chip 31 and a plurality of aligned rings of different colored LED lights 81, 82, and 83 encircling the aperture 33; 2) a middle camera filter unit 72 with the light filters 37, 38 within the rotatable 36 and fixed 39 housing; and 3) a lens unit 74 comprising a rear camera lens 43 and CMOS imager unit 44, a rear PCB 42, and a battery 50 to power the entire camera unit. Other arrangements of the different types of LED lights are envisioned within the scope of the present invention.

The LED PCB 34 comprises a gyroscope chip 31 that is used to detect whether the assembly 100 is being handheld, or is sitting at rest in the slit-lamp. The gyroscope samples the rate of rotation of the camera unit in the x, y, and z axis, at 100 hertz, which is filtered by a bandpass filter on the LED PCB. If the output in the filter is detected by the processor to exceed a designated threshold, then the camera is determined to be handheld, and the mobile application running on the clinician's electronic computing device will adjust image capture accordingly.

In another embodiment (not shown), the camera PCB 34 or 42, further comprises a wireless transmitter chip (e.g. Bluetooth®, Wi-Fi, etc.) to: transmit computer code instructions (e.g. for operation of camera, operation of mobile application on computer, etc.); and to transmit camera images (photographs and/or videos) to the clinician's electronic computing device, and/or to a remote server for storage in a patient's record.

Figure 5A:
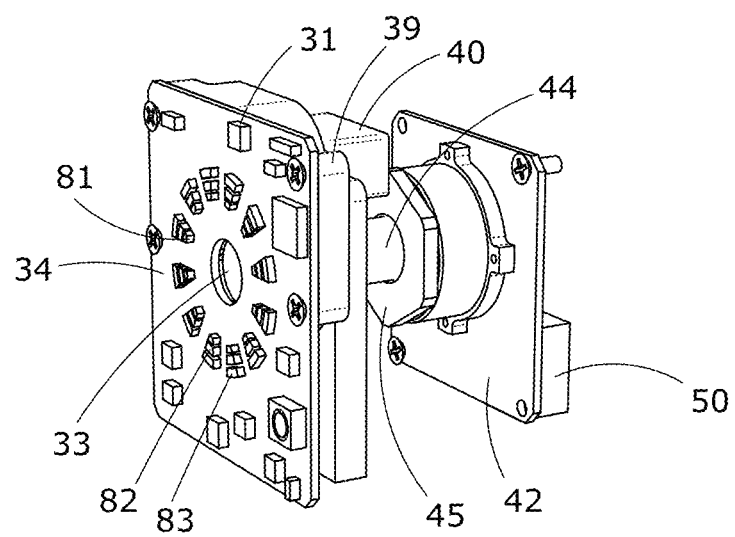
FIG. 5A is a front perspective view of the optical system that is housed within the camera unit.
Figure 5B:
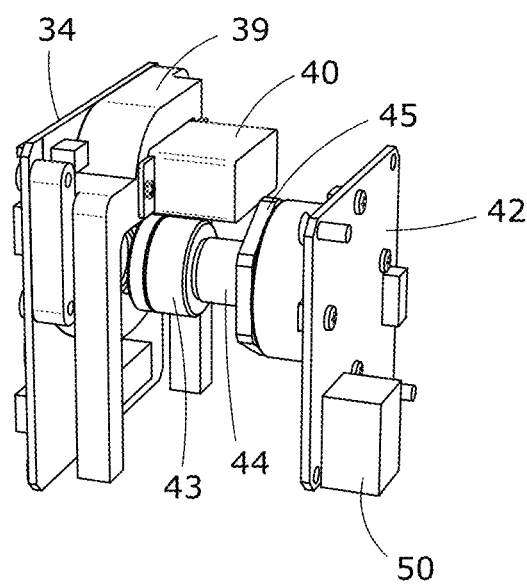
FIG. 5B is a rear perspective view of FIG. 5A comprising the optical system.
Figure 5C:
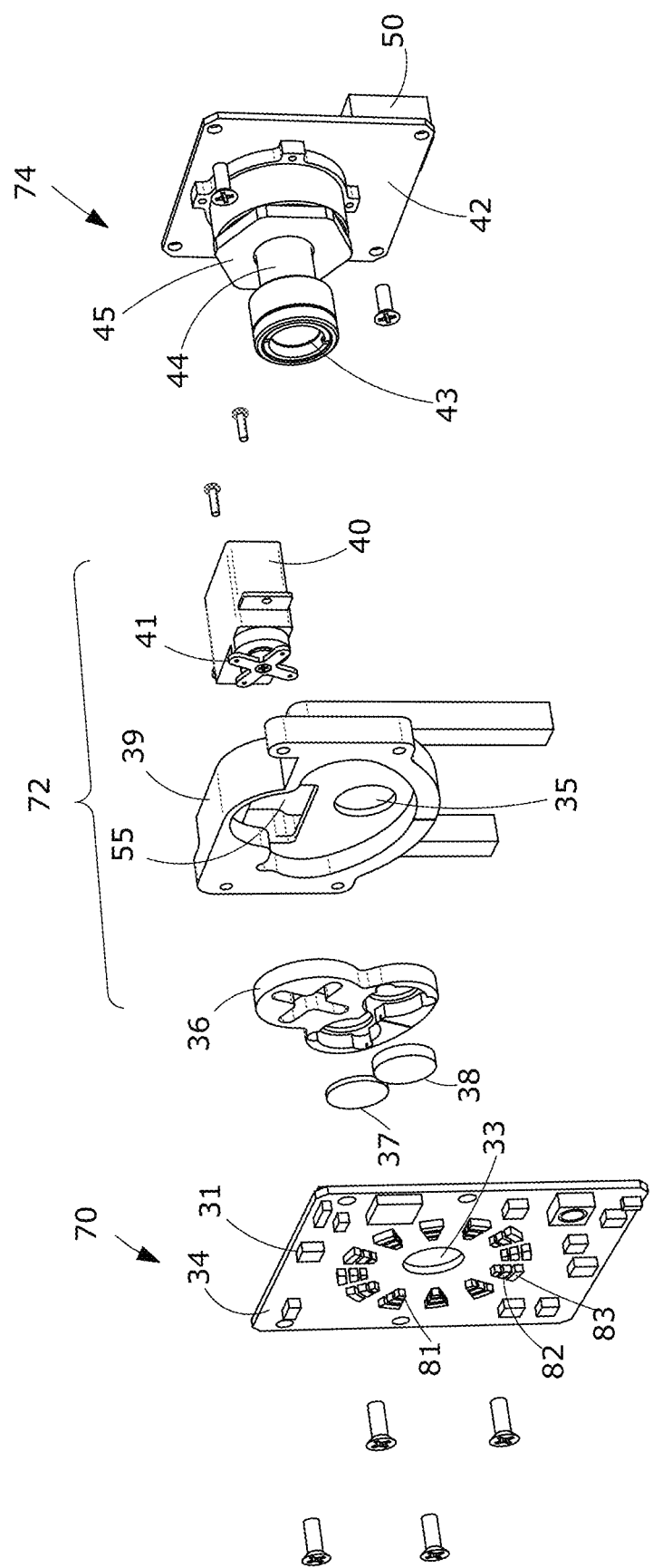
FIG. 5C is an exploded view of the optical system of FIG. 5A; and illustrating the two filters: Infrared (IR) light and longer wavelengths, and visible light and shorter wavelengths.
Figure 5D:
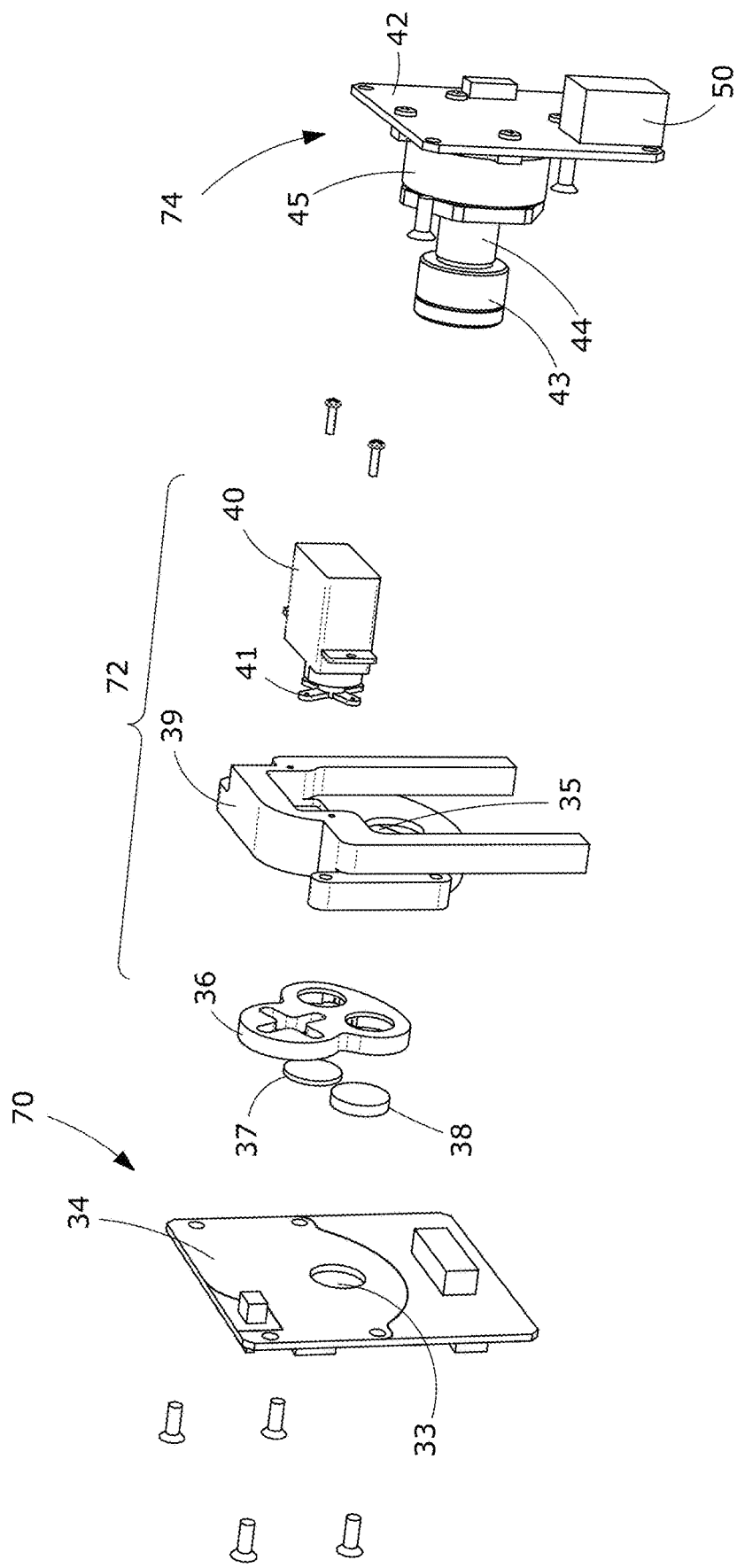
FIG. 5D is an exploded side view of the optical system of FIG. 5B.
Figure 5E:
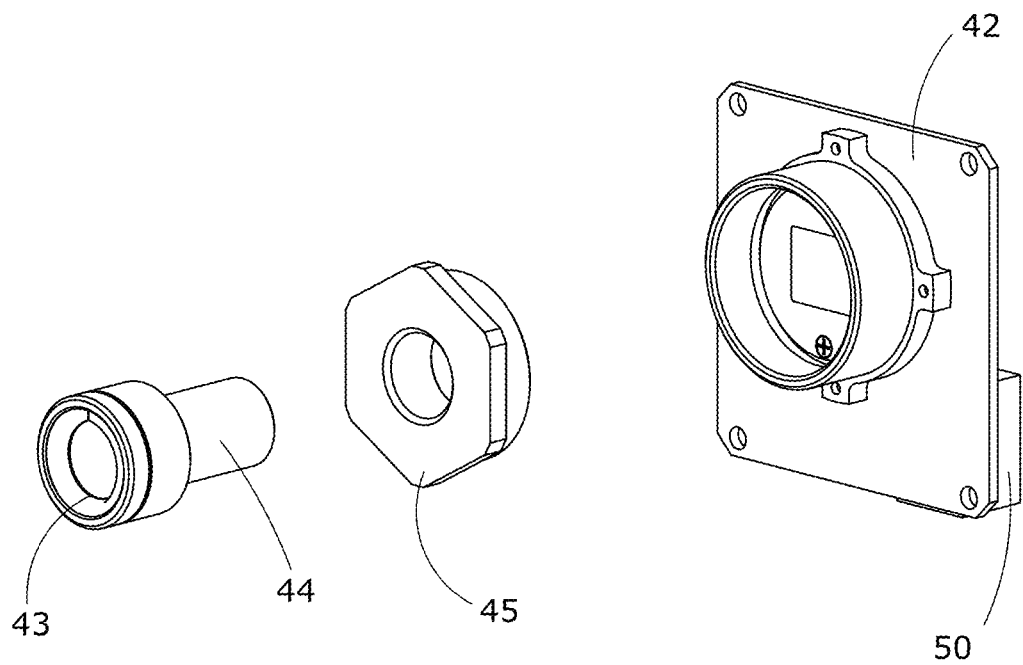
FIG. 5E is an exploded view of the camera lens subassembly.

As illustrated in FIGS. 5A and 5C, the front PCB 34 also comprises three rings of aligned LEDs, from inner to outer rings of: warm white lights 81, blue lights 82 and infrared light 83. The present invention has significant advantages over the prior art by enabling the recording of images using three different types of light, which can be used to diagnose different medical conditions/disorders: 1) capture visible light; 2) capture infrared (IR) light; and 3) capture visible light without the blue light.

The middle camera filter unit 72 further comprises: two glass filters 37, 38; housed in a rotatable holder 36, that is rotated by a servo 40 using propeller 41 under the operational control of, e.g., the mobile application on the clinician's electronic computing device. Rotatable holder 36 resides within the fixed filter housing 39 with a substantially shaped half-circular aperture 55 for fitting the servo propeller 41. Fixed housing 39 further comprises a circular opening 35 aligned with the rear camera lens 43. A loose coupling is used between the servo 40 and the rotatable holder 36 to compensate for any non-orthogonality between servo 40 and the fixed housing 39.

Filter 37 cuts out the infrared light and longer wavelengths from the captured images; and filter 38 cuts out the visible light and shorter wavelengths from the captured images. The filters are rotated into position in front of camera lens 43, which is a fixed focal length lens.

Lens 43 is positioned in front of a complementary metal oxide semiconductor (CMOS) sensor 44, which converts photons to electrons for digital processing, and uses a Bayer color filter well known in the art. The printed circuit board (PCB) 42 transmits camera operational commands from the mobile application to the lens/filters/CMOS sensor, and the captured images to the clinician's computer and/or a remote server for storage. And the battery 50 powers the camera unit, and in an embodiment, is user replaceable.

Eye Image Recording System

As used herein, the term "A System" may be used to claim all, or parts of, the aspects of the present disclosure wherein it refers to the entire configuration, or parts of the networked based system, e.g. all hardware and software used in all scenarios. Preferred embodiments are illustrated in the system architecture of FIG. 6A.

As used herein, the terms "Processing," "Computing," "Calculating," "Determining," "Establishing", "Analyzing", "Checking", or the like, may refer to operation(s) and/or process(es) of a computer, a computing platform, a computing system, a computer central processing unit (CPU), or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Figure 6A:
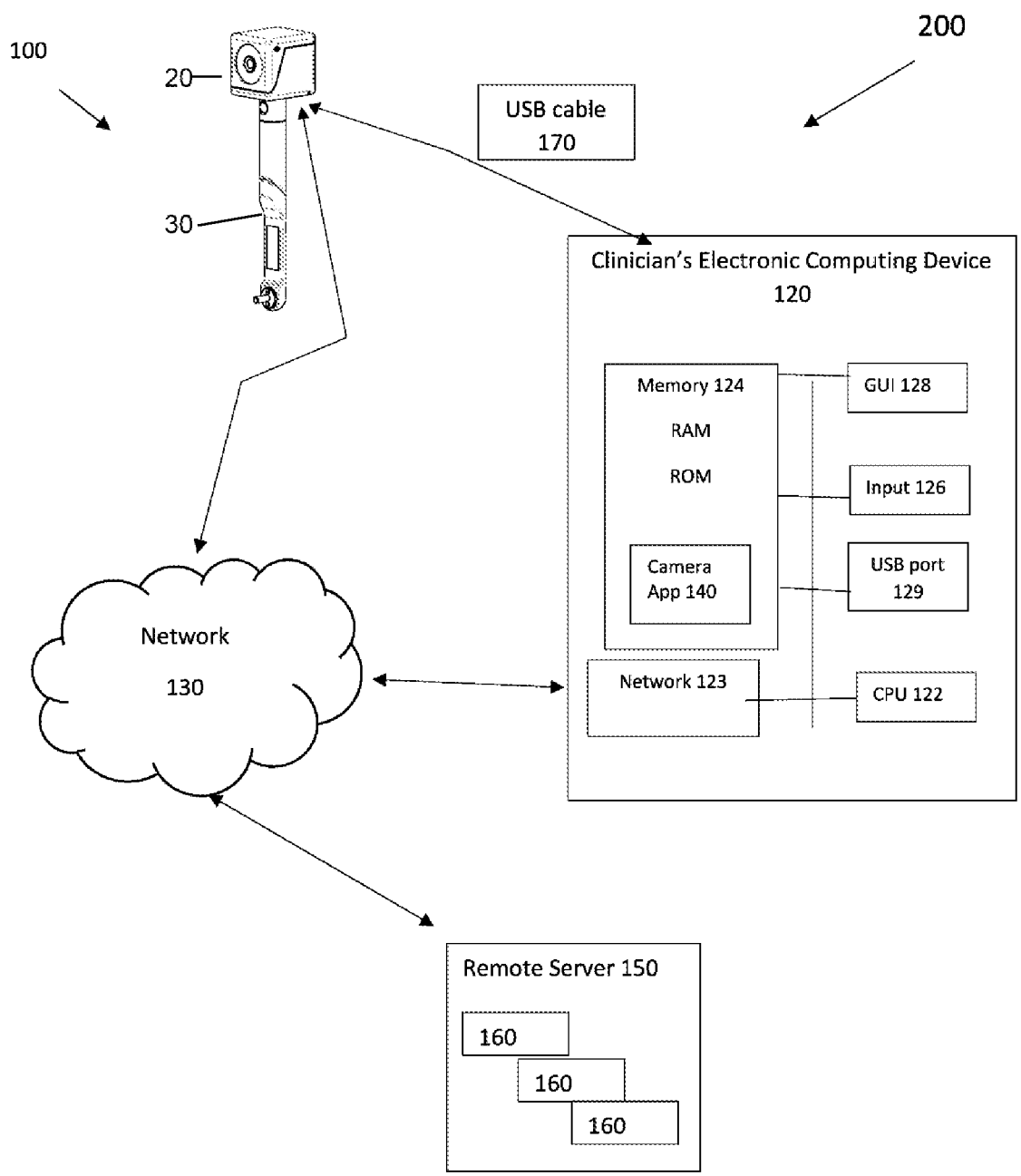
FIG. 6A is a block diagram of a networked system of the present invention comprising the camera-pivotable handle assembly in communication with a clinician's electronic computing device to transmit and store eye images in a patient's medical record.

As illustrated in FIG. 6A, the present invention further comprises an eye recording networked system comprising: 1) a camera-pivotable arm assembly 100; and 2) a clinician's electronic computing device 120 having stored thereon, or accessible via a network 130, a mobile application 140 to control the camera 20 and store the images. In an embodiment, the system may further comprise: 3) a wireless network 130 for transmitting captured images to the device 120 and/or to 4) a remote server 150 to store in a patient's medical records 160.

The clinician electronic computing device 120 (e.g. laptop, tablet, desktop PC, smartphone, PDA, etc.) comprises: one or more processing units (CPUs) 122; a USB port 123; one or more memories 124; user input devices—keyboard & mouse, touchscreen—126; a graphical user interface (GUI) 128; and a wired or wireless network connection 129.

Kits: if the clinician's device 120 is within reach of the camera assembly 100, then the USB cable 170 is used to connect the two. If not, then the kit of the present invention is used to connect the two. The kit comprises: a transmitter, a receiver, a power adapter and an Ethernet cable. The user connects the transmitter to the clinician's device 120 using USB cable 170; then connects the receiver to the power (e.g. wall outlet) using the power adapter; then connects one end of the ethernet cable to the transmitter and the other end to the receiver; and connects the camera/arm assembly 100 to the receiver using the USB cable 170.

Clinician Examination—Method of Use

The present invention further comprises the camera software 140 that runs on the clinician electronic computing device 120 (e.g. laptop) to take patient histories, control operation of the camera, take videos and/or photographs of the patient's inner and outer eyes, and edit the images if needed, and save the results.

As used herein, the term "Software" refers to computer program instructions adapted for execution by a hardware element, such as a processor or CPU, wherein the instruction comprise commands that when executed cause the processor to perform a corresponding set of commands. The software may be written or coded using a programming language, and stored using any type of non-transitory computer-readable medium or machine-readable medium well known in the art. Examples of software in the present disclosure comprise any software components, programs, applications, computer programs, application programs, system programs, machine programs, and operating system software.

Figure 6B:
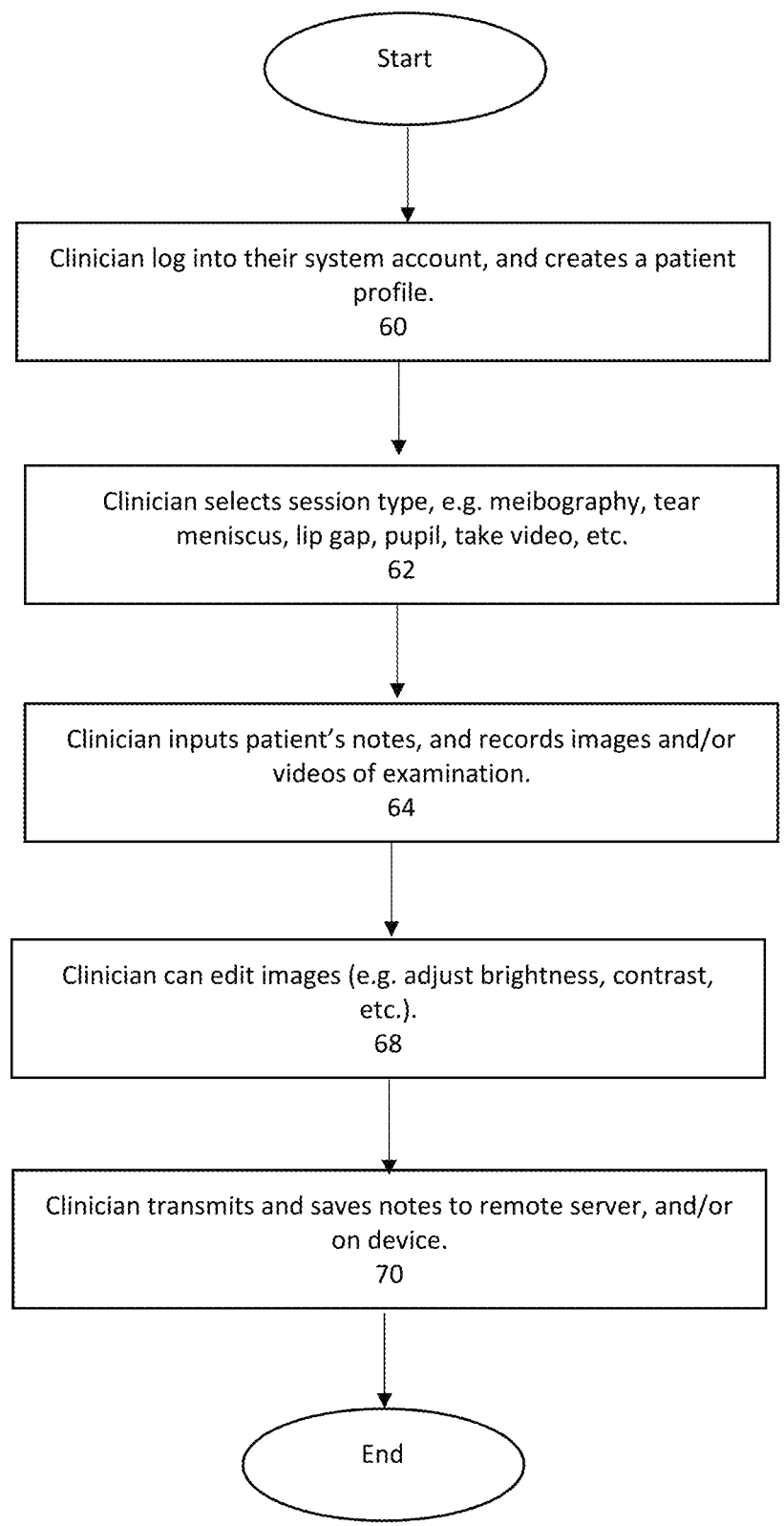
FIG. 6B is a flowchart of computer steps performed in using the camera-pivotable handle assembly of the present invention to capture and store images of a patient's eye on a clinician's electronic computing device, or a remote server.

FIG. 6B is a flowchart of exemplary steps followed by a clinician in using software 140, which is a computer program product, comprising: a non-transitory computer-readable storage device having computer-readable program instructions embodied thereon that when executed by a computer cause the computer to transmit and store camera images, the computer-executable program instructions comprising, by way of a non-limiting example: computer program instructions to carry out the steps of FIG. 6B using the system 200 of FIG. 6A.

In step 60, the clinician, or their assistant, logs into the software application 140, which is either installed on device 120, or accessible via a network. The clinician can also create a new digital record 160 for a new patient, or open and update the record of an existing patient.

In step 62, the clinician selects the type of examination they would like to perform, such as by way of non-limiting examples: meibography; measuring one or more of a tear meniscus, a lip gap, a pupil size, etc.; take video and/or photograph; etc.

In step 64, the clinician inputs their patient's notes, and records images and/or videos of examination. Methods of inputting of data may comprise one or more of: typing in notes, audio input that is converted to text using transcription software well known in the art, audio input that is recorded as voice input, etc.

In step 68, the clinician has the ability to edit the images if required (e.g. adjust brightness, contrast, etc.).

In step 70, the clinician transmits via network 130 and saves their notes and images on remote server 150 in a patient's digital record 160. Additionally, or alternatively, the notes and images can be saved in memory of the clinician's device 120.

CONCLUSION

It will be appreciated that the methods and compositions and compounds of the present disclosure can be incorporated in the form of a variety of embodiments, only a few of which are disclosed herein. It will also be apparent for the expert skilled in the field that other embodiments exist and do not depart from the spirit of the invention. Thus, the described embodiments are illustrative and should not be construed as restrictive.

Accordingly, the preceding exemplifications merely illustrate the principles of the various embodiments. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the various embodiments, therefore, is not intended to be limited to the exemplary embodiments shown and described herein.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Or, the technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 5%), and use of the term "about" at the beginning of a string of values modifies each of the values (i.e., "about 1, 2 and 3" refers to about 1, about 2 and about 3). Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

As used herein, the term "substantially" refers to approximately the same shape as stated.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments.

Trademarks: the product names used in this document are for identification purposes only; and are the property of their respective owners.

What is claimed is:

1. A clinician eye image recording apparatus, comprising:
    a) a camera unit comprising an outer housing, and internal components comprising:
        1) a front printed circuit board (PCB) comprising,
            i) a middle aperture in the front PCB able to fit a rear camera lens;
            ii) a plurality of light emitting diodes (LEDs) encircling the middle aperture comprising aligned rings of: a warm white light LED, a blue light LED, and an infrared light LED, positioned to enable the camera unit to capture light from the warm white light LED, the blue light LED, and the infrared light LED;

2) a middle camera filter unit, comprising a plurality of light filters, and a servo motor with a propeller that rotates one of the light filters into position in front of a rear camera lens;

3) a rear camera lens connected to a complementary metal oxide semiconductor (CMOS) sensor, a rear printed circuit board (PCB), and a battery;

b) a pivotable arm assembly comprising:
1) a top end unit attachable to the camera unit, the top end unit comprising a recording button to activate and deactivate the camera unit to record eye images by transmitting commands to the rear printed circuit board; and
2) a middle handle unit pivotably attached to an arm unit.

2. The image recording apparatus of claim 1, wherein the arm unit is rotatable from a first position aligned with the middle handle unit for a clinician to hold and move the apparatus, and to a second position with the arm unit rotated until it is perpendicular to the middle handle unit.

3. The image recording apparatus of claim 2, wherein an apparatus bottom end of the arm unit further comprises at least one adapter to enable the bottom end to attach to a slit lamp accessory mounting hole.

4. The eye image recording apparatus of claim 1, wherein the front printed circuit board (PCB) further comprises a gyroscope to determine if the apparatus is handheld and moving, or is in a fixed position as mounted in a slit lamp.

5. The eye image recording apparatus of claim 1, wherein the plurality of light filters in the middle camera filter unit comprise: an infrared filter and a white light filter.

6. The eye image recording apparatus of claim 1, further comprising a filter rotatable holder housing the plurality of light filters and positioned within a fixed filter housing, wherein the plurality of light filters is rotatable within the fixed filter housing to align with the rear camera lens.

7. The eye image recording apparatus of claim 1, wherein the fixed filter housing further comprises a top aperture and a middle aperture, the top aperture houses for the servo propeller, and the middle aperture aligns with the rear camera lens and one of the light filters.

8. A networked system to allow a clinician to capture and store eye camera images, comprising:
a) a camera unit comprising an outer housing, and internal components comprising:
1) a front printed circuit board (PCB) comprising,
i) a middle aperture in the front PCB able to fit a rear camera lens;
ii) a plurality of light emitting diodes (LEDs) encircling the middle aperture comprising aligned rings of: a warm white light LED, a blue light LED, and an infrared light LED, positioned to enable the camera unit to capture light from the warm white light LED, the blue light LED, and the infrared light LED;
2) a middle camera filter unit, comprising a plurality of light filters, and a servo motor with a propeller that rotates one of the light filters into position in front of a rear camera lens;
3) a rear camera lens connected to a complementary metal oxide semiconductor (CMOS) sensor, a rear printed circuit board (PCB), and a battery;

b) a pivotable arm assembly comprising:
1) a top end unit attachable to the camera unit, the top end unit comprising a recording button to activate and deactivate the camera unit to record eye images by transmitting commands to the rear printed circuit board; and
2) a middle handle unit pivotably attached to an arm unit;

c) a clinician's electronic computing device comprising a memory or storage device, and a processor communicatively coupled to the storage device, wherein the processor executes application code instructions that are stored in the storage device to cause the system to: select a camera lens, capture camera images of a patient's eye, and store the images; and d) a network connection between a recording apparatus and the clinician's device comprising one or more of: a USB cable, and/or a wireless network; and e) a remote cloud-based server to store the camera images within a patient's digital file.

9. The networked system of claim 8, wherein the arm unit is rotatable from a first position aligned with the middle handle unit for a clinician to hold and move the apparatus, and to a second position with the arm unit rotated until it is perpendicular to the middle handle unit.

10. The networked system of claim 8, wherein an apparatus bottom end of the arm unit further comprises at least one adapter to enable the bottom end to attach to a slit lamp accessory mounting hole.

11. The networked system of claim 8, wherein the front printed circuit board (PCB) further comprises a gyroscope to determine if the apparatus is handheld and moving, or is in a fixed position as mounted in a slit lamp.

12. The networked system of claim 8, wherein the plurality of light filters in the middle camera unit comprise: an infrared filter and a white light filter.

13. The networked system of claim 8, further comprising a filter rotatable holder housing the plurality of light filters and positioned within a fixed filter housing, wherein the plurality of light filters is rotatable within the fixed filter housing to align with the rear camera lens.

14. The networked system of claim 8, wherein the fixed filter housing further comprises a top aperture and a middle aperture, the top aperture houses for the servo propeller, and the middle aperture aligns with the rear camera lens and one of the light filters.

15. A method of diagnosing and treating a patient with an eye disorder, comprising:
1) providing a clinician eye image recording apparatus, comprises:
a) a camera unit comprising an outer housing, and internal components comprising:
i) a front printed circuit board (PCB) comprising,
a middle aperture in the front PCB able to fit a rear camera lens;
a plurality of light emitting diodes (LEDs) encircling the middle aperture comprising aligned rings of: a warm white light LED, a blue light LED, and an infrared light LED, positioned to enable the camera unit to capture light from the warm white light LED, the blue light LED, and the infrared light LED;
ii) a middle camera filter unit, comprising a plurality of light filters, and a servo motor with a propeller that rotates one of the light filters into position in front of a rear camera lens;

iii) a rear camera lens connected to a complementary metal oxide semiconductor (CMOS) sensor, a rear printed circuit board (PCB), and a battery;
b) a pivotable arm assembly comprising:
  i) a top end unit attachable to the camera unit, the top end unit comprising a recording button to activate and deactivate the camera unit to record eye images by transmitting commands to the rear printed circuit board; and
  ii) a middle handle unit pivotably attached to an arm unit
2) connecting a clinician electronic computing device to the recording apparatus using a USB cable or a wired or wireless network connection;
3) activating a non-transitory computer storage medium on the clinician device and selecting a type of eye examination;
4) activating the camera unit to capture and transmit camera images to the clinician electronic computing device; and
5) diagnosing and treating the patient based upon the camera images, a physical examination and a patient history.

16. The method of claim 15, wherein the arm unit is rotatable from a first position aligned with the middle handle unit for a clinician to hold and move the apparatus, and to a second position with the arm unit rotated until it is perpendicular to the middle handle unit.

17. The method of claim 15, wherein an apparatus bottom end of the arm unit further comprises at least one adapter to enable the bottom end to attach to a slit lamp accessory mounting hole.

18. The method of claim 15, wherein the front printed circuit board (PCB) further comprises a gyroscope to determine if the apparatus is handheld and moving, or is in a fixed position as mounted in a slit lamp.

19. The method of claim 15, wherein the plurality of light filters comprise: an infrared filter and a white light filter.

20. The method of claim 15, further comprising in the middle camera filter unit:
a) a filter rotatable holder containing the plurality of light filters and positioned within a fixed filter housing;
b) the fixed filter housing comprising a top aperture and a middle aperture, the top aperture housing the servo propeller, and the middle aperture aligning with the rear camera lens; and
c) wherein the plurality of light filters is able to rotate within the fixed filter housing to align one light filter with the middle aperture and the rear camera lens.

* * * * *